(12) United States Patent
Yamanaka et al.

(10) Patent No.: US 8,632,882 B2
(45) Date of Patent: Jan. 21, 2014

(54) DIALKOXYMAGNESIUM GRANULES AND METHOD FOR THEIR SYNTHESIS

(75) Inventors: Akihiko Yamanaka, Gyoda (JP); Hiroshi Kumai, Gyoda (JP); Mitsuteru Suyama, Gyoda (JP)

(73) Assignee: Colcoat Co., Ltd., Tokyo (JP)

( * ) Notice: Subject to any disclaimer, the term of this patent is extended or adjusted under 35 U.S.C. 154(b) by 346 days.

(21) Appl. No.: 12/226,119

(22) PCT Filed: Mar. 23, 2007

(86) PCT No.: PCT/JP2007/057012
§ 371 (c)(1),
(2), (4) Date: Oct. 7, 2008

(87) PCT Pub. No.: WO2007/116815
PCT Pub. Date: Oct. 18, 2007

(65) Prior Publication Data
US 2009/0202833 A1    Aug. 13, 2009

(30) Foreign Application Priority Data
Apr. 7, 2006 (JP) .................. 2006-105781

(51) Int. Cl.
*B32B 1/00* (2006.01)
*C07C 41/01* (2006.01)
(52) U.S. Cl.
USPC ......................................... 428/402; 568/672
(58) Field of Classification Search
None
See application file for complete search history.

(56) References Cited

U.S. PATENT DOCUMENTS

| 6,855,656 B2 * | 2/2005 | Hosaka et al. ............... 502/118 |
| 2005/0227857 A1 | 10/2005 | Tanase et al. |
| 2008/0188687 A1 | 8/2008 | Tanase et al. |

FOREIGN PATENT DOCUMENTS

| CN | 1656050 A | 8/2005 | |
| EP | 1 283 222 A1 | 2/2003 | |
| EP | 1 775 309 A1 | 4/2007 | |
| JP | 3-74341 | 3/1991 | |
| JP | 7-20898 | 3/1995 | |
| JP | 08-073388 | 3/1996 | |
| JP | 2001-233879 | 8/2001 | |
| JP | 2002-356507 | 12/2002 | |
| JP | 2003-342217 | 12/2003 | |
| JP | 2004-210683 | 7/2004 | |
| JP | 2006199739 | 8/2006 | |
| JP | 2006274105 | 10/2006 | |
| WO | WO 02081527 | * 10/2002 | ............ C08F 210/06 |

(Continued)

OTHER PUBLICATIONS

International Search Report, dated May 1, 2007, corresponding to PCT/JP2007/057012.

(Continued)

*Primary Examiner* — Yun Qian
(74) *Attorney, Agent, or Firm* — Christie, Parker & Hale, LLP

(57) ABSTRACT

Dialkoxymagnesium granules having spherical or ellipsoidal particle shapes with a mean particle size, represented by D50, in the range of 60-200 μm, a bulk specific gravity of 0.2-0.7 g/ml, having numerous interior pores with pore sizes of 0.1-5 μm as observed with a TEM, and having a particle size distribution, represented by $(D_{90}-D_{10})/D_{50}$, of no greater than 1. Granular metallic magnesium and an alcohol are added continuously or intermittently in divided portions to a reaction system of the metallic magnesium and alcohol while circulating the alcohol for reaction. Large-sized dialkoxymagnesium granules are obtained with a uniform particle size distribution and containing no fine powder.

2 Claims, 3 Drawing Sheets

(56) References Cited

FOREIGN PATENT DOCUMENTS

| WO | WO 2006/013876 A1 | 2/2006 |
| WO | WO 2006/033512 A1 | 3/2006 |
| WO | WO 2007/026017 | 3/2007 |

OTHER PUBLICATIONS

Patent Abstracts of Japan, Publication No. 03074341 A, Published on Mar. 28, 1991, in the name of Nomura, et al.
Patent Abstracts of Japan, Publication No. 03-074341 A, Published on Mar. 28, 1991, in the name of Nomura, et al.
Patent Abstracts of Japan, Publication No. 2001233879 A, Published on Aug. 28, 2001, in the name of Tanase, et al.
Patent Abstracts of Japan, Publication No. 2003342217 A, Published on Dec. 3, 2003, in the name of Tanase, et al.
Patent Abstracts of Japan, Publication No. 2004-210683 A, Published on Jul. 29, 2004, in the name of Hosaka, et al.
EP Search Report for application No. 07740450.7, dated Apr. 12, 2011, in the name of Colcoat Co., Ltd., 8 pages.
Office action for corresponding Japanese Patent Application No. 2007-047861, dated May 29, 2012, 6pp.
Office action for corresponding Chinese patent application No. 200780012538.2, dated Sep. 23, 2011, 5pp.

* cited by examiner

US 8,632,882 B2

DIALKOXYMAGNESIUM GRANULES AND METHOD FOR THEIR SYNTHESIS

CROSS-REFERENCE TO RELATED APPLICATION

This application is a National Phase Patent Application and claims the priority of International Application Number PCT/JP2007/057012, filed on Mar. 23, 2007, which claims priority of Japanese Patent Application Number 2006 -105781, filed on Apr. 7, 2006.

TECHNICAL FIELD

The present invention relates to dialkoxymagnesium granules used for preparation of a solid catalyst component for olefin polymerization, and to a method for their synthesis.

BACKGROUND ART

Dialkoxymagnesiums, especially diethoxymagnesium, are used as solid catalyst components for polymerization of olefins such as propylene. Spherical or ellipsoidal diethoxymagnesium is used, and although the mean particle size, represented by $D_{50}$, is known in patent documents to be 10-100 μm, in practice it is no greater than 50 μm. This is because increasing the mean particle size lowers the catalyst strength and results in problems such as micronization during use.

It is known that using an olefin polymerization catalyst obtained using diethoxymagnesium granules yields an olefin polymer with a shape that is enlarged and analogous to the catalyst shape. Therefore, a spherical catalyst shape also produces a spherical polymer. The obtained polymer preferably has a spherical shape for a superior flow property, but the polymerization catalyst must then have a spherical shape as well, and therefore it is important for the shape of the diethoxymagnesium as the catalyst component to also be spherical.

The particle shapes of olefin polymers obtained using polymerization catalysts employing diethoxymagnesium particles with particle sizes of about 50 μm are enlarged and analogous to the shape of the catalyst, but such polymers are in the form of fine powder which are still too small for direct molding with molding machines such as injection molding machines. The polymer fine powder obtained by such polymerization is therefore pelletized before being molded into a product. If the olefin polymer obtained by polymerization could be used for direct molding without passing through a pelletizing stage (step), to obtain a usable product, significant value in terms of cost would be achieved. It is therefore necessary to obtain diethoxymagnesium as spheres or ellipsoids with particle sizes of 80 μm or greater and preferably 100 μm or greater, and with a narrow particle size distribution range.

Methods for obtaining spherical dialkoxymagnesium by direct reaction between metallic magnesium and an alcohol have long been known and are described in, for example, Japanese Examined Patent Publication HEI No. 7-20898. In recent years, improved methods have been proposed wherein spherical dialkoxymagnesium obtained in the manner described above is contacted with an alkoxytitanium compound in an inert organic solvent to form a suspension and the solvent is then removed (Japanese Unexamined Patent Publication No. 2004-210683).

However, it is difficult to obtain spherical dialkoxymagnesium of a large enough size to eliminate the need for pelletizing of olefin polymers, and even when a large size is obtained the strength is extremely low. When an olefin polymerization catalyst is prepared using dialkoxymagnesium with such insufficient strength as the starting material, the starting material disintegrates during the preparation process, making it impossible to obtain a large-sized catalyst with uniform shapes. The polymer obtained using such a catalyst with non-uniform shapes will also have non-uniform particle sizes and a larger proportion of fine powder, while a larger proportion of the polymer will be non-spherical and the flow property will be impaired.

Also, the diethoxymagnesium production processes proposed in the prior art yield products whose content of fine particles with sizes of less than 1-10 μm is 5-8 mass % or greater of the total product. Because such particles form fine catalysts even after catalyst preparation, fine polymer powder is also abundantly present in the polymers obtained from them, and it interferes with the flow property. Consequently, diethoxymagnesium with a mean particle size of no greater than 50 μm and containing particles with fine particle sizes of no greater than 10 μm are used at the current time, even though it is desired to increase the particle size and minimize the presence of fine particles.

DISCLOSURE OF THE INVENTION

It is an object of the present invention to solve the problems mentioned above by providing large-sized dialkoxymagnesium granules with a uniform particle size distribution and containing no fine powder, as well as a method for their synthesis.

Specifically, the invention achieves this object by the following construction.

(1) Dialkoxymagnesium granules with a narrow particle size distribution, having spherical or ellipsoidal particle shapes with a mean particle size, represented by $D_{50}$, in the range of 60-200 μm, a bulk specific gravity of 0.2-0.7 g/ml, having numerous interior pores with pore sizes of 0.1-5 μm as observed with a TEM, and having a particle size distribution, represented by $(D_{90}-D_{10})/D_{50}$, of no greater than 1.

(2) Dialkoxymagnesium granules according to (1) above, which have numerous micropores with a mean pore size of 0.1-50 nm as calculated from the specific surface area and pore volume determined from the BJH adsorption pore distribution, and wherein the volume of the micropores is 0.01-0.5 cm³/g.

(3) Dialkoxymagnesium granules according to (1) or (2) above, which essentially contain no particles with particle sizes of less than 10 μm.

(4) Dialkoxymagnesium granules according to any one of (1) to (3) above, which consist of porous aggregates of spherical, ellipsoidal, scaly or needle-like dialkoxymagnesium primary particles having particle sizes of 1-10 μm.

(5) Dialkoxymagnesium granules according to any one of (1) to (4) above, wherein the $N_2$ adsorption BET specific surface area is 50-500 m²/g.

(6) Dialkoxymagnesium granules according to any one of (1) to (5) above, wherein the breaking strength of the aggregated granules is 0.5-10 MPa.

(7) A method for synthesis of dialkoxymagnesium granules having spherical or ellipsoidal particle shapes with a mean particle size, represented by $D_{50}$, in the range of 60-200 μm, a bulk specific gravity of 0.2-0.7 g/ml, having numerous interior pores with pore sizes of 0.1-5 μm as observed with a TEM, and having a particle size distribution, represented by $(D_{90}-D_{10})/D_{50}$, of no greater than 1, wherein for synthesis of dialkoxymagnesium by reaction between metallic magnesium and an alcohol, the final use proportion of metallic magnesium and alcohol in the reaction system is 1/4-1/25 in terms of mass ratio, metallic magnesium having a particle size of no greater than 500 μm and alcohol are added continuously or intermittently in divided portions to the reaction system while circulating the alcohol, and the reaction is conducted for 100-1200 minutes.

(8) A synthesis method according to (7) above, wherein the dialkoxymagnesium granules have numerous micropores with a mean pore size of 0.1-50 nm as calculated from the specific surface area and pore volume determined from the BJH adsorption pore distribution, and wherein the volume of the micropores is 0.01-0.5 cm$^3$/g.

(9) A synthesis method according to (7) or (8) above, wherein addition of the metallic magnesium and alcohol is divided into 10 or more portions, the intervals of addition being a combination of any desired intervals in the range of 10-120 minutes, with a total addition time of no greater than 1200 minutes.

According to the invention it is possible to obtain large-sized dialkoxymagnesium granules with a uniform particle size distribution and containing no fine powder, and by conducting olefin polymerization using an olefin polymerization catalyst comprising the granules as the catalyst component, it is possible to obtain an olefin polymer with particle sizes large enough to eliminate the need for a pelletizing step before molding process.

More specifically, the dialkoxymagnesium granules of the invention are spherical or ellipsoidal with a narrow particle size distribution, having a larger mean particle size than in the prior art and with no fine powder, and wherein the numerous pores in the interior have relatively large sizes, with a mean pore size of 0.1-5 μm. Apart from these pores, it also preferably has numerous micropores of 0.1-50 nm, with a volume of 0.01-0.5 cm$^3$/g for these micropores. Even with an olefin polymerization catalyst using these granules as the catalyst component, it is possible to obtain particle sizes of 80-100 μm which will allow production of an olefin polymer containing minimal fine powder or coarse powder and with particle sizes large enough to eliminate the need for a pelletizing step during molding.

BEST MODE FOR CARRYING OUT THE INVENTION

Figure 1:
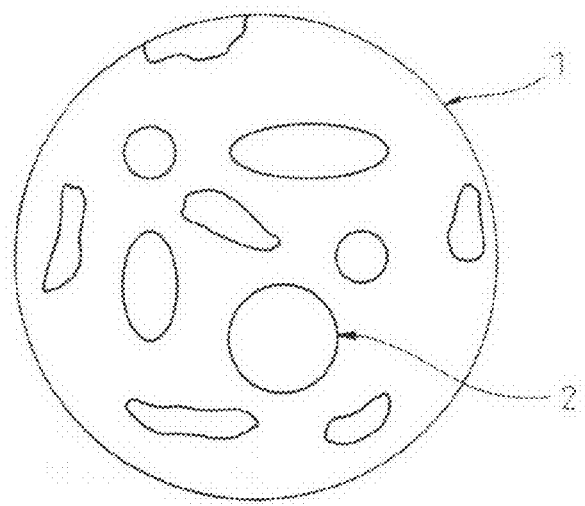
FIG. 1 is a cross-sectional schematic drawing of granular particles according to the invention.

Preferred modes of the invention will now be explained in detail with the understanding that the invention is not limited only to these modes, and various modifications may be implemented that are within the spirit and scope of the invention.

The $D_{10}$, $D_{50}$ and $D_{90}$ values used for the invention are well known to those skilled in the art, and they represent particle sizes at 10%, 50% and 90% of the integrated particle sizes, respectively. Specifically, for example, $D_{10}$ is the particle size at which the integrated value for the mass of the granules in measurement of the grain size distribution of the granules is 10 mass %. Thus, $D_{50}$ represents the median particle size for the granules as a whole, and therefore the mean particle size.

The large-sized dialkoxymagnesium granules of the invention may consist of porous aggregates of spherical, ellipsoidal, scaly or needle-like dialkoxymagnesium primary particles having particle sizes of 1-10 μm, but preferably they contain essentially no particles with particle sizes of less than 10 μm. The pores with pore sizes of 0.1-5 μm inside the granules as observed with a TEM (transmission electron microscope) are believed to be the gaps between particles, produced when the primary particles aggregate as described above. If the gaps between particles exceed 5 μm the bonding between primary particles will be weak, resulting in insufficient strength of the granules.

The large-sized dialkoxymagnesium granules of the invention preferably have numerous micropores with a mean pore size of 0.1-50 nm as calculated from the specific surface area and pore volume determined from the BJH adsorption pore distribution, in addition to the pores conjectured to be the aforementioned gaps between the primary particles, with the volume of the micropores being 0.01-0.5 cm$^3$/g. The micropores may be distributed numerously within each of the primary particles forming the granules of the invention. "BJH" referred to here is the abbreviation for Barrett-Joyner-Halenda, and the method is described in detail in E. P. Barrett, L. G. Joyner, P. P. Halenda; J. Am. Chem. Soc. 73, 373 (1951).

The particle size distribution of the dialkoxymagnesium granules of the invention is calculated by the formula ($D_{90}$–$D_{10}$)/$D_{50}$, and it is a very narrow distribution of 1 or smaller. Granules with such a narrow particle size distribution also have a narrow particle size distribution of catalyst particles when the olefin polymerization catalyst has been formed, and the granular olefin polymer obtained using the catalyst will also have a narrow particle size distribution and therefore a satisfactory flow property. Similar particle sizes for the catalyst particles will also increase the reaction rate for olefin polymerization, thus improving the polymer productivity. Furthermore, since the catalyst essentially contains no fine powder, the polymerization takes place without reaction failures and less fine-powdered polymer is obtained, thus avoiding the risk of explosion during handling of the polymer. In addition, since fewer coarse grains are present, the flow property of the polymer is not easily reduced.

In the dialkoxymagnesium granules of the invention, the specific surface area as measured by the $N_2$ adsorption BET method is preferably in the range of 50-500 m$^2$/g, and the breaking strength of the granules is preferably in the range of 0.5-10 MPa. In addition, the bulk specific gravity is in the range of 0.2-0.7 g/ml and preferably in the range of 0.3-0.5 g/ml.

Such spherical or ellipsoidal dialkoxymagnesium granules may be synthesized by reaction between metallic magnesium and an alcohol for 100-1200 minutes specifying an final use proportion of metallic magnesium and alcohol in the reaction system of 1/4-1/25 in terms of mass ratio, wherein granular metallic magnesium and alcohol are added continuously or intermittently in divided portions to the reaction system while circulating the alcohol, the reaction preferably being followed by aging reaction. The dialkoxymagnesium granules obtained in this manner may be used as the catalyst component to prepare a catalyst for olefin polymerization.

According to the invention, metallic magnesium granules with particle sizes of no greater than 500 μm are used as the starting material. The granules are preferably fine particles with a mean particle size, represented by $D_{50}$, of 50-500 μm and a particle size distribution, represented by ($D_{90}$–$D_{10}$)/$D_{50}$, of no greater than 2. The granules in this case may be in a powder form. They may also be in a form obtained by shaving an ingot of magnesium metal. The reaction between the magnesium metal and alcohol may be carried out while hydrogen is generated, in which case it is preferred to minimize the degree of oxidation of the surfaces of the magnesium metal particles. Therefore, they are preferably kept in an atmosphere of an inert gas such as nitrogen, or protected from surface oxidation by treatment of the metal surface with a solvent that does not affect the reaction.

The alcohol used for the invention is preferably one with a C1-5 alkyl group, and most preferred is ethyl alcohol. The water content of the alcohol is preferably as low as possible. The use proportion at the final point of the reaction between the metallic magnesium and alcohol must be 1/4-1/25 in terms of mass ratio. The reaction that occurs is alkoxylation of metallic magnesium. When the reaction is carried out with circulation of an alcohol, this alcohol is also included in the "alcohol" according to the invention. If the amount of alcohol is less than 4 times the amount of metallic magnesium, the reaction will not proceed sufficiently and unreacted magnesium may remain, thus making it impossible to achieve control to the intended particle size. If it exceeds 25, the product particles formed by the reaction will include a large amount of alcohol and numerous gaps will be created when the alcohol escapes by drying, thus preventing the intended bulk specific gravity from being achieved.

A catalyst is preferably used for the synthesis method of the invention, and as useful catalysts there may be mentioned alkyl halides, metal halides, dialkoxymagnesiums and iodine, which are preferably used at 0.5-15 mass % with respect to the metallic magnesium. The catalyst may be added initially all at once to the reaction system, or it may be added while adjusting the amount according to the divided addition of the starting material.

The addition of the metallic magnesium and alcohol to the reaction system is preferably carried out continuously or in at least 10 separate portions, over a period of 100-1200 minutes. The object of the invention may not be achieved by addition all at once or in only 4-5 divided portions. In other words, according to the invention it is preferred to add the starting material in such a manner that synthesis reaction only proceeds after the primary particles of dialkoxymagnesium produced in the reaction system have become attached to the dialkoxymagnesium already present in the system. The interval between the divided addition will vary depending on the size of the reactor, the temperature and other conditions, but it is preferably 10-120 minutes. That is, dialkoxymagnesium is produced from the reaction after the divided addition in earlier stages, and the next starting material addition is preferably made at the stage after the $H_2$ generation has almost completely ended (at the stage when almost no unreacted metallic magnesium remains).

The divided addition of the starting material to the reaction system is carried out with circulation of an alcohol solvent, preferably the same alcohol as the starting material, and it may be in any desired manner. For example, the metallic magnesium and alcohol may be added in order at a prescribed interval in the same proportion as the final use proportion, or they may be added while gradually increasing the amount of addition. Alternatively, they may be added in divided portions in a starting material ratio that differs from the final use proportion. For example, the proportion of metallic magnesium may be increased at the start of the reaction to above the final use proportion, and the proportion of metallic magnesium reduced in the latter stages. With divided addition, it is generally preferred for the amount of metallic magnesium to be in the range of 2-50 mass % with respect to the amount of alcohol added. In any case, the next portion of the magnesium is preferably added upon essential completion of the reaction of the previously added magnesium, for a final ratio of both starting materials in the range of 1/4-1/25 by mass. The reaction time is a total of 100-1200 minutes, and completion of the reaction is judged as the point at which hydrogen is no longer generated.

After the final addition of the starting materials, and after hydrogen is no longer generated, the product is preferably aged at a temperature between 70° C. and the reflux temperature of the solvent, for stabilization of the product particles. The time may be varied as appropriate depending on the desired particle size and particle size distribution and on the bulk specific gravity. The temperature during aging may be between 70° C. and the reflux temperature of the solvent, the stirring speed is 50-500 rpm, but the temperature and stirring speed may be selected according to the desired particle size and particle size distribution and the bulk specific gravity.

The $D_{50}$ particle size of the dialkoxymagnesium granules obtained in this manner, particularly diethoxymagnesium particles, is in the range of 60-200 μm, and the granules may have large sizes of 80-200 μm, which will permit elimination of a pelletizing step during molding of olefin polymers produced using the polymerization catalyst. The particle sizes have a uniform distribution, the particle size distribution, represented by $(D_{90}-D_{10})/D_{50}$, being no greater than 1. In addition, very few fine particles with sizes of less than 10 μm are present in the product, the content being less than 1 mass % which is essentially equivalent to absence thereof.

The dialkoxymagnesium granules obtained as described above preferably have a porous structure consisting of aggregates of controlled spherical, ellipsoidal, scaly or needle-like primary particles with sizes of 1-10 μm, and the sizes of the pores composing the porous structure are 0.1-5 μm based on TEM observation. The granules preferably have numerous micropores thought to exist in the primary particles of which they are composed, where the mean pore size of the micropores is 0.1-50 nm and the volume of the micropores is 0.01-0.5 cm³/g. The bulk specific gravity is in the range of 0.2-0.7 g/ml. FIG. 1 is a schematic drawing showing cross-sections 2 of distribution pores as seen by TEM observation of a cross-section of a diethoxymagnesium granular particle 1 obtained according to the invention, wherein the pore sizes of the pores are in the range of 0.1-5 μm.

In order to prepare a catalyst for olefin polymerization using the dialkoxymagnesium granules of the invention as starting material, a tetravalent titanium halide and an electron-donating compound are contacted with the dialkoxymagnesium granules by a known method to form a catalyst component, and an organic aluminum compound is reacted therewith. As tetravalent titanium halides there may be mentioned titanium tetrachloride and alkoxytitanium halides, and as electron-donating compounds there may be mentioned alcohols, ethers, esters and organic silicon compounds such as alkoxysilanes. As aluminum compounds there may be mentioned triethylaluminum and diethylaluminum chloride.

The present invention will now be explained in greater detail by examples and comparative examples, with the understanding that the invention is in no way limited to these examples. The "parts" referred to throughout the examples are parts by mass.

EXAMPLE 1

After $N_2$ substitution of a reactor equipped with an $H_2$ flow rate gas meter, reflux condenser, thermometer and stirring blade, 168.3 parts of ethyl alcohol was added and the mixture was stirred at 250 rpm, room temperature. After then adding 2.1 parts of iodine as a catalyst and 1 part of metallic magnesium granules ($D_{50}$ particle size: 128 μm) and 8.5 parts of ethyl alcohol as starting materials, stirring was continued for 30 minutes at room temperature. An oil bath was then used to raise the temperature, and reaction was conducted for 15 minutes which circulating the alcohol. Next, 2.0 parts of metallic magnesium granules and 8.5 parts of ethyl alcohol were added 12 times at 30 minute intervals under the same conditions, and after the final addition of starting material, reaction was conducted for 20 minutes, 32.8 parts of ethyl alcohol was further added, reaction was continued for 80 minutes while circulating the alcohol, and the reaction was completed upon confirming that $H_2$ generation had ceased. The total amount of metallic magnesium addition was 25 parts, the total amount of ethyl alcohol used was 311.6 parts, the mass ratio was 1/12.5, and the total reaction time was 490 minutes.

The obtained reaction mixture was transferred to a rotary evaporator, and the ethyl alcohol was distilled off under conditions of 60° C., 100 mmHg to obtain 118 parts of dried diethoxymagnesium particles. The $D_{50}$ particle size of the obtained product (granules) was 85.5 μm, the $D_{10}$ particle size was 56.3 μm, the $D_{90}$ particle size was 130.9 μm and the particle size distribution, represented by $(D_{90}-D_{10})/D_{50}$, was 0.87. The product contained virtually no fine powder with particle sizes of 10 μm or smaller, and exhibited a very sharp particle size distribution. Observation with a scanning electron microscope (SEM) revealed essentially spherical shapes, with a bulk specific gravity of 0.32 g/ml (measured according to JIS K-51011-12-1(2004)). The particle sizes and particle size distribution were measured using a MICROTRAC MT-3200 (product of Nikkiso Co., Ltd.).

Figure 2:
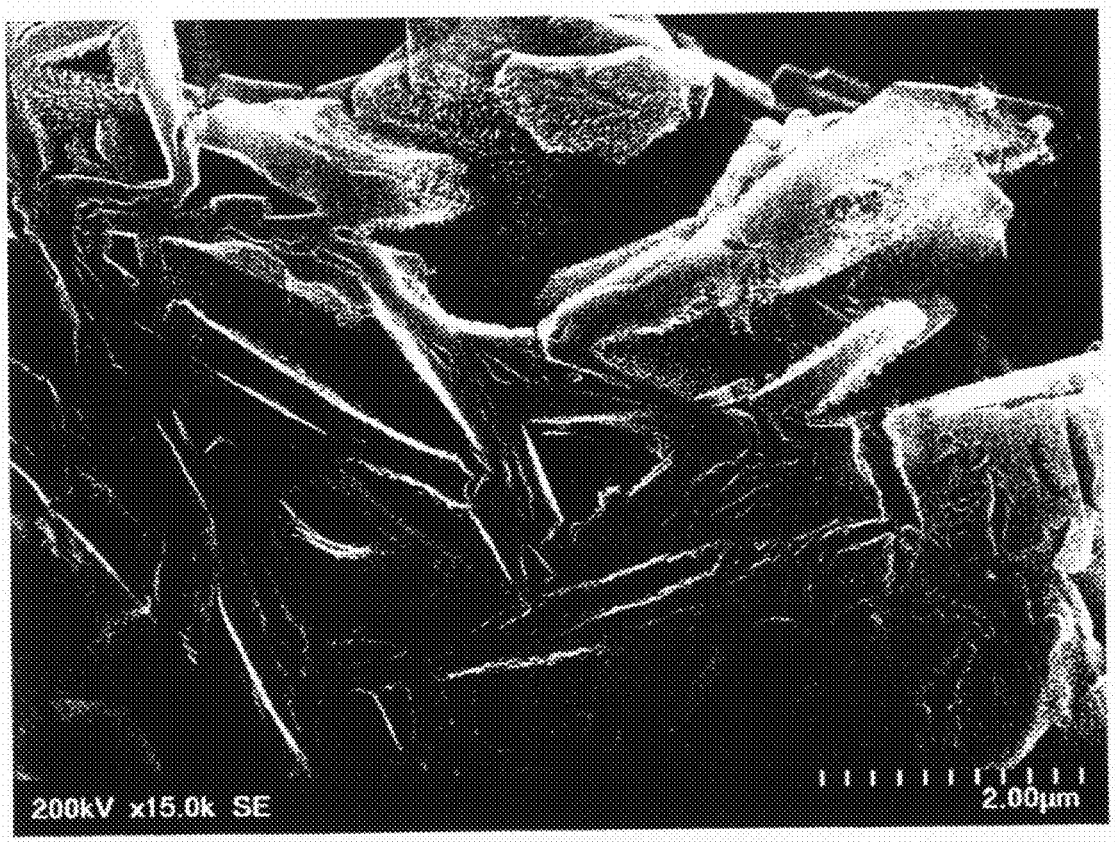
FIG. 2 is a TEM image of the diethoxymagnesium particles obtained in Example 1.

FIG. 2 is a TEM image taken with an HF-2200TU transmission electron microscope by Hitachi, Ltd., after FIB treatment of the diethoxymagnesium particles obtained in the manner described above, using an FB-2000A (Hitachi Focused Ion Beam observer by Hitachi High-Tech Science Systems). "FIB" stands for Focused Ion Beam, and the method involves irradiating the sample with a gallium ion beam to cut the sample to produce a cut surface for easier TEM observation, and in this case the irradiation was at an acceleration voltage of 30 kV. The photograph shows that the pore cross-sections had different shapes but had pore sizes limited in the range of 0.5-3 μm.

EXAMPLE 2

The procedure was conducted essentially in the same manner as Example 1. However, after the metallic magnesium and ethyl alcohol had been added for the initial charging and reaction had been conducted for 15 minutes with circulation, subsequent addition was divided into 24 portions at 20 minute intervals with the amount of metallic magnesium addition at 1 part each and the amount of ethyl alcohol addition at 8.5 parts each. After the final addition of starting material, reaction was conducted for 80 minutes while circulating the alcohol, and reaction was completed upon confirming no further generation of $H_2$. The total amounts of metallic magnesium addition and ethyl alcohol used were the same, their use proportion (mass ratio) was 1/12.5, and the total reaction time was 570 minutes. The reaction mixture was transferred to a rotary evaporator, and the ethyl alcohol was distilled off under conditions of 60° C., 100 mmHg to obtain 118 parts of dried diethoxymagnesium particles. The granules had a $D_{50}$ particle size of 105.8 μm, a $D_{10}$ particle size of 74.8 μm, a $D_{90}$ particle size of 157.3 μm, and a particle size distribution, represented by $(D_{90}-D_{10})/D_{50}$, of 0.78. The product contained absolutely no fine powder with particle sizes of 10 μm or smaller, and exhibited a very narrow particle size distribution.

Also, SEM observation revealed essentially spherical shapes, with a bulk specific gravity of 0.28 g/ml. As a result of observing the obtained diethoxymagnesium particles with a TEM in the same manner as Example 1, the pore cross-sections were found to have different shapes, but the pore sizes were limited to a range of 0.3-2.5 μm.

The granules contained numerous micropores separately from these pores, and their mean pore sizes were 2.6 nm, with a micropore volume of 0.23 cm$^3$/g. The specific surface area measured by the $N_2$ adsorption BET multipoint method was 264 m$^2$/g. The specific surface area was determined by a BET plot (data for relative pressure and cumulative adsorption). The particle breaking strength of the granules was 1.0 MPa.

For Example 2, the mean pore size of the micropores is the value obtained using the specific surface area and micropore volume as determined by the BJH adsorption pore distribution (measured using a TriStar3000 automatic specific surface area/pore distribution measuring apparatus by Shimadzu Corp.). The micropore volume is the value determined from the BJH adsorption pore distribution (analysis range: 1-100 nm). The breaking strength was measured using a MCT-W Series Microcompression Tester by Shimadzu Corp., under conditions with a test force of 100 mN and a load speed of 12.9 mN/sec.

Figure 4:
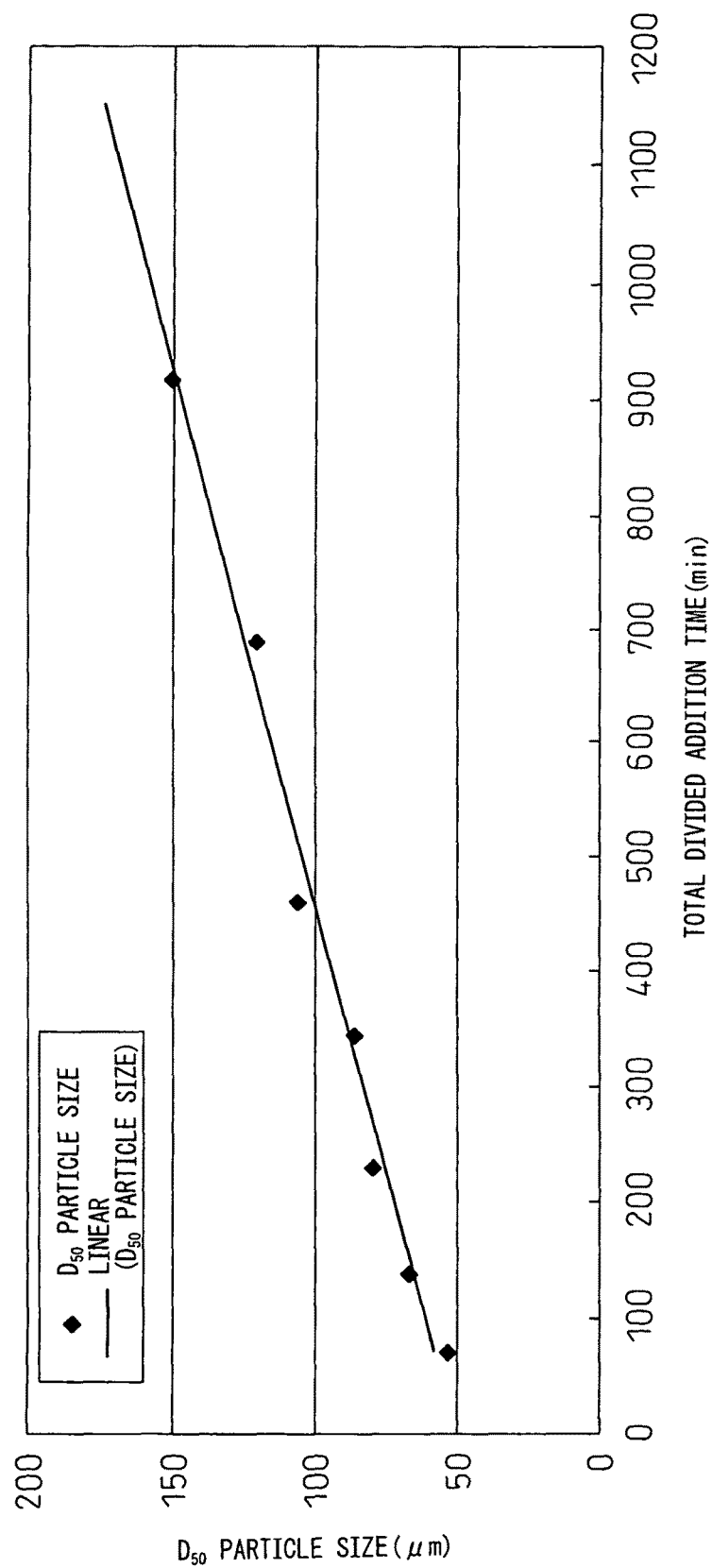
FIG. 4 is a graph showing the relationship between total divided addition time and resulting $D_{50}$ particle size.

Upon varying the interval for addition of the portions in Example 2, a linear relationship was observed between the total divided addition time and the $D_{50}$ particle size of the diethoxymagnesium produced, as shown in FIG. 4. This indicates that the desired $D_{50}$ particle size can be obtained by controlling the total divided addition time.

EXAMPLE 3

Using the same apparatus as in Example 1, with 261.8 parts of ethyl alcohol as the charged solvent, 0.1 part of metallic magnesium granules and 10.8 parts of ethyl alcohol were added for the initial charging after stabilizing the rotational speed, and 2.1 parts of iodine was added as the catalyst, after which the mixture was stirred at room temperature for 30 minutes. An oil bath was then used to raise the temperature to the reflux temperature of the alcohol, and reaction was conducted for 15 minutes. Next, metallic magnesium was added, varying the amount of each addition between 0.1-3.0 parts (0.1 part for the first portion, with gradual stepwise increase from 0.1 part to 0.2 part, and addition of 3 parts for the final 11th portion), for a total use of 25 parts including the initially charged metallic magnesium. The alcohol was added in a total of 11 portions of 5.4 parts each at 10 minute intervals, and after the final addition of starting material, reaction was conducted for 20 minutes, 32.8 parts of ethyl alcohol was further added, reaction was continued for 80 minutes while circulating the alcohol, and the reaction was completed upon confirming that $H_2$ generation had ceased. The final use proportion (mass ratio) of metallic magnesium/alcohol was 1/14.6, and the total reaction time was 230 minutes. The rest of the procedure was carried out as in Example 1 to obtain 117 parts of dried diethoxymagnesium particles.

Figure 3:
FIG. 3 is a TEM image of the particles obtained in Example 3.

The obtained granules were composed of roughly spherical particles according to SEM observation, with a $D_{50}$ particle size of 84.7 μm and a particle size distribution, represented by $(D_{90}-D_{10})/D_{50}$, of 0.94, and virtually no fine powder with sizes of less than 10 μm was present, while a very sharp distribution was exhibited. The bulk specific gravity was 0.33 g/ml. A TEM image of the obtained diethoxymagnesium particles is shown in FIG. 3. Here it is seen that pores with pore sizes limited to about 0.2-1 μm are present. Measurement by the analysis method described in Example 2 indicated that numerous micropores were present in the granules, with mean pore sizes of 2.5 nm and a micropore volume of 0.25 cm$^3$/g. The area-to-mass ratio measured by the N$_2$ adsorption BET multipoint method was 120 m$^2$/g. The particle breaking strength of the granules was 3.0 MPa.

EXAMPLE 4

After conducting reaction for 15 minutes with the first circulation in the same manner as Example 3, the addition interval was changed to 30 minutes and a total of 11 additions were carried out. After the final addition, reaction was continued for 100 minutes with circulation. The total reaction time was 430 minutes, and the final use proportion (mass ratio) of metallic magnesium/ethyl alcohol starting material was 1/14.6. The obtained diethoxymagnesium particles had a $D_{50}$ particle size of 140.7 μm and a particle size distribution, represented by $(D_{90}-D_{10})/D_{50}$, of 0.99, while virtually no fine powder with sizes of less than 10 μm was present and a very sharp distribution was exhibited. The bulk specific gravity was 0.27 g/ml.

As a result of observing the obtained diethoxymagnesium particles by TEM observation in the same manner as Example 1, the pore cross-sections were found to have different shapes, but the pore sizes were limited to a range of 0.3-3.5 μm.

EXAMPLE 5

Using the same apparatus as in Example 1, with 261.8 parts of ethyl alcohol as the charged solvent, 0.1 part of metallic magnesium granules and 11.0 parts of ethyl alcohol were added for the initial charging after stabilizing the rotational speed, and 2.1 parts of iodine was added as the catalyst, after which the mixture was stirred at room temperature for 30 minutes. An oil bath was then used to raise the temperature to the reflux temperature of the alcohol, and reaction was conducted for 15 minutes. Next, metallic magnesium was added, varying the amount of each addition between 0.1-2.2 parts (0.1 part for the first portion, with gradual stepwise increase 0.1 part at a time, and addition of 2.2 parts for the final 22nd portion), for a total use of 25.4 parts including the initially charged metallic magnesium. The alcohol was added in a total of 22 portions of 5.5 parts each at 10 minute intervals, and after the final addition of starting material, reaction was conducted for 20 minutes, 32.8 parts of ethyl alcohol was further added, reaction was continued for 80 minutes while circulating the alcohol, and the reaction was completed upon confirming that H$_2$ generation had ceased. The final use proportion (mass ratio) of metallic magnesium/alcohol was 1/17.9, and the total reaction time was 374 minutes. The rest of the procedure was carried out as in Example 1 to obtain 120.4 parts of dried diethoxymagnesium particles. The obtained granules were composed of roughly spherical particles according to SEM observation, with a $D_{50}$ particle size of 97.4 μm and a particle size distribution, represented by $(D_{90}-D_{10})/D_{50}$, of 0.86, and virtually no fine powder with sizes of less than 10 μm was present, and a very sharp distribution was exhibited. The bulk specific gravity was 0.33 g/ml.

As a result of observing a TEM image of the obtained diethoxymagnesium particles in the same manner as Example 1, the pore cross-sections were found to have different shapes, but the pore sizes were limited to a range of 1.0-3.5 μm. Numerous micropores smaller than these pores were also present in the granules, and measurement by the analysis method described in Example 2 indicated their mean pore size was 4.8 nm, the specific surface area by the BET multipoint method was 67 m$^2$/g, and the micropore volume was 0.08 cm$^3$/g. The particle breaking strength was 2.2 MPa.

COMPARATIVE EXAMPLE

Using the same apparatus as in Example 1, with 136.1 parts of ethyl alcohol as the charged solvent, 5.0 parts of metallic magnesium granules and 34.0 parts of ethyl alcohol were added for the initial charging after stabilizing the rotational speed, and 2.1 parts of iodine was added as the catalyst, after which the mixture was stirred at room temperature for 30 minutes. An oil bath was then used to raise the temperature to the reflux temperature of the alcohol, and reaction was conducted for 15 minutes. Next, portions of 4.0 parts of metallic magnesium and 17.0 parts of ethyl alcohol were added a total of 5 times at 6 minute intervals, and after the final addition of magnesium, reaction was conducted for 20 minutes and the reaction was completed upon confirming that hydrogen generation had ceased. The total reaction time was 59 minutes, and the added magnesium/alcohol mass ratio was 1/11.5. The reaction solution was aged for 80 minutes, and then a product was obtained in the same manner as Example 1. The obtained diethoxymagnesium particles were roughly spherical, the $D_{50}$ particle size was 38.5 μm, the particle size distribution, represented by $(D_{90}-D_{10})/D_{50}$, was 1.69, and the content of fine powder with sizes of less than 10 μm was greater than 10 mass %. The bulk specific gravity was 0.25 g/ml.

Industrial Applicability

The dialkoxymagnesium obtained according to the invention is useful as a component for an olefin polymerization catalyst.

The invention claimed is:

1. Dialkoxymagnesium granules with a narrow particle size distribution, having spherical or ellipsoidal particle shapes with a mean particle size, represented by $D_{50}$, in the range of 60-200 μm, a bulk specific gravity of 0.2-0.7 g/ml, having numerous interior pores with pore sizes of 0.1-5 μm as observed with a TEM, and having a particle size distribution, represented by $(D_{90}-D_{10})/D_{50}$, of no greater than 1, and consisting of porous aggregates of spherical, ellipsoidal, scaly or needle-like dialkoxymagnesium primary particles having particle sizes of 1-10 μm.

2. Dialkoxymagnesium granules with a narrow particle size distribution, having spherical or ellipsoidal particle shapes with a mean particle size, represented by $D_{50}$, in the range of 60-200 μm, a bulk specific gravity of 0.2-0.7 g/ml, having numerous interior pores with pore sizes of 0.1-5 μm as observed with a TEM, and having a particle size distribution, represented by $(D_{90}-D_{10})/D_{50}$, of no greater than 1, and having a breaking strength of 0.5-10 MPa.

* * * * *